United States Patent
Wong et al.

(10) Patent No.: US 6,239,191 B1
(45) Date of Patent: May 29, 2001

(54) DENTURE ADHESIVE COMPRISING A POLYMERIC ACTIVATOR AND METHODS OF PREPARING THE SAME

(75) Inventors: Eddie Wong, New Providence, NJ (US); Hal C. Clarke, Elmont, NY (US); Robert C. Gasman, Montville, NJ (US); Alfred J. Smetana, Wayne, NJ (US); Joseph Synodis, Summit, NJ (US)

(73) Assignee: Block Drug Company, Inc., Jersey City, NJ (US)

( * ) Notice: Subject to any disclaimer, the term of this patent is extended or adjusted under 35 U.S.C. 154(b) by 0 days.

(21) Appl. No.: 09/255,905

(22) Filed: Feb. 23, 1999

Related U.S. Application Data

(62) Division of application No. 08/880,592, filed on Jun. 23, 1997, now Pat. No. 6,025,441.
(51) Int. Cl.[7] ................................ A61K 5/06; C08L 35/08
(52) U.S. Cl. .......................... 523/120; 433/180; 523/118; 524/517; 524/522; 524/549
(58) Field of Search ................................... 523/118, 120; 433/180; 524/517, 522, 549

(56) References Cited

U.S. PATENT DOCUMENTS 4,521,551 * 6/1985 Chang et al. .
4,910,247 * 3/1990 Haldar et al. .
5,525,652 * 6/1996 Clarke et al. .

* cited by examiner

Primary Examiner—Peter A. Szekely

(57) ABSTRACT

A denture adhesive composition is disclosed and comprises a polymeric activator in an amount of up to about 3 percent by weight based on the total weight of the denture adhesive composition. This composition exhibits enhanced adhesive performance and reduces oozing and incidence of food occlusion. Also disclosed is a method of preparing a denture adhesive composition comprising: preparing a mixture which comprises a polymeric activator in an amount of up to about 3 percent by weight based on the total weight of the denture adhesive composition; forming a denture adhesive composition including the mixture; and recovering the denture adhesive composition. A method of making a denture adhesive composition more adhesive and less oozing is disclosed as well. This method comprises adding to the denture adhesive composition a polymeric activator in an amount of up to about 3 percent by weight based on the total weight of the denture adhesive composition.

7 Claims, No Drawings

DENTURE ADHESIVE COMPRISING A POLYMERIC ACTIVATOR AND METHODS OF PREPARING THE SAME

This is a division of application Ser. No. 08/880,592, filed Jun. 23, 1997. Now U.S. Pat. No. 6,025,411.

BACKGROUND OF THE INVENTION

1. Field of the Invention

The present invention relates to denture adhesives containing a polymeric activator, such as a polymeric acid, and to methods of improving a denture adhesive product by adding a polymeric activator.

2. Description of the Related Art

Dentures are substitutes for missing teeth and serve as replacement for all or some of the teeth found in the oral cavity. Despite diligent efforts by dental professionals and designers of dental prostheses, dentures do not always fit perfectly. Over time, even well-fitting dentures can become ill-fitting due to natural shrinkage and changes in the gum or mucous tissues. Therefore, adherent creams, liquids or powders are often used to secure dentures within the mouth.

There are a number of desirable characteristics of a denture fixative composition. One extremely desirable attribute is that it develops a high degree of tack upon contact with saliva so that the dentures can be held in place as soon as they are seated in the mouth. It is also highly desirable that the mucilage be spread over the denture-mucosa interface in order to effectively seal the denture in place and that the mucilages possess sufficient cohesive strength to withstand the stresses of mastication which act to rupture the seal and thus dislodge the denture. The denture fixative must also exhibit sufficient resistance to degradation under the extreme environmental changes that occur in the oral cavity during such common actions as drinking coffee or other hot beverages. Of course, the adhesive must also be releasable so that the denture wearer may remove the dentures for cleaning and maintenance. Denture adhesives are generally sold as a cream, liner or strip, liquid or powder, and many examples are well known in the art.

Early denture adhesives contained finely ground particles of natural gums that expanded when wet with water to become a viscous gel, which acted as a cushion and an adherent between the denture plate and the gum tissue. These denture adhesives, however, have tended to be supplanted by polymeric denture adhesives.

U.S. Pat. No. 3,003,988, for example, describes a dental fixative composition in which the dental fixative is a mixed partial salt containing calcium cations and alkali or quaternary ammonium cations of a lower alkyl vinyl ether-maleic anhydride type copolymer. The mixed salt copolymer is stated to be a water-insoluble, but water sensitized, copolymer.

U.S. Pat. No. 3,736,274 teaches a dental fixative composition that contains a lower alkyl vinyl ether-maleic anhydride polymeric material, a polymeric N-vinyl lactam and a sodium carboxymethyl cellulose. The carboxymethyl cellulose prevents the lower alkyl vinyl ether-maleic anhydride copolymer-N-vinyl lactam complex from completely precipitating when placed in water.

U.S. Pat. No. 3,868,432 teaches an anhydrous denture adhesive composition that is a mixture of a copolymer of an acrylamide and an anionic synthetic gum component which can be a copolymer of maleic acid with vinyl lower alkyl ether.

U.S. Pat. No. 4,373,036 discloses a denture fixative composition containing hydroxypropyl cellulose and a partially neutralized, optionally crosslinked, polyacrylic acid or a precursor combination thereof, or partially neutralized copolymers of maleic acid or anhydride and alkyl vinyl ethers which are optionally partially crosslinked, or a precursor combination thereof, and/or polyethylene oxide.

U.S. Pat. No. 4,521,551 discloses a denture fixative composition containing denture fixative excipients and as the denture fixative, a water soluble partially neutralized alkyl vinyl ether-maleic acid or anhydride copolymer, optionally partly crosslinked with a polyhydroxyl compound, and at least one hydrophilic polymer, preferably sodium carboxymethyl cellulose, polyethylene oxide or hydroxy propyl sugar.

U.S. Pat. No. 4,758,630 discloses denture adhesives comprising zinc and strontium partial salts of lower alkyl vinyl ether-maleic acid copolymers, wherein the zinc and strontium cations are unmixed with any other cations or ester functions in the copolymeric salt, the remaining initial carboxyl group being unreacted.

U.S. Pat. No. 5,006,571 discloses denture adhesives comprising a substantially anhydrous mixture of a mixed Na/Ca salt of methyl vinyl ether-maleic acid, sodium carboxymethyl cellulose, and a trivalent cation. Dihydroxy aluminum sodium carbonate may be the source of the trivalent cation. Dihydroxy aluminum sodium carbonate may be the source of the trivalent cation, in which case a food grade acid must be added to aid in release of the aluminum from the composition. Exemplary acids include citric acid, malic acid, tartaric acid, and fumaric acid. The acid may comprise up to about 4 percent by weight of the denture adhesive composition. Additionally, benzoic acid or sorbic acid may be included in the denture adhesive as a preservative.

U.S. Pat. Nos. 5,525,652 and 5,830,933 disclose the use of mixed copolymer acid salts in the formulation of denture adhesive compositions. Preferably the salts are mixed salts of Ca/Na or Ca/K, and most preferably they are partial Zn/Mg salts and Na/Zn/Mg salts. The disclosure of each of these is hereby incorporated by reference.

U.S. Pat. No. 5,093,387 also discloses that benzoic acid and sorbic acid may be used as preservatives in denture adhesive formulations in amount of about 0.03 to about 0.6 percent by weight of the total denture adhesive composition.

Each of the denture adhesive materials discussed above has certain advantages and disadvantages when compared with other denture adhesives. The search for better denture adhesive materials continues, however, and denture adhesives with better hold, longer hold and better organoleptic properties are always desirable.

SUMMARY OF THE INVENTION

It is the object of this invention to provide new and improved denture fixatives that exhibit enhanced adhesive performance and reduced oozing and incidence of food occlusion.

This and other objects of the invention will become apparent to those skilled in the art from the following detailed description.

The present invention provides a denture adhesive composition comprising a polymeric activator in an amount of up to about 3 percent by weight based on the total weight of the denture adhesive composition.

The present invention further provides a method of preparing a denture adhesive composition comprising: preparing a mixture that comprises a polymeric activator in an amount of up to about 3 percent by weight based on the total weight of the denture adhesive composition; forming a denture adhesive composition including said mixture; and recovering said denture adhesive composition.

The present invention further provides a method of making a denture adhesive composition more adhesive and less oozing, comprising adding to said denture adhesive composition a polymeric activator in an amount of up to about 3 percent by weight based on the total weight of the denture adhesive composition.

DETAILED DESCRIPTION OF THE INVENTION

A novel denture adhesive base composition with surprisingly good performance has been discovered. Specifically, denture adhesives of the present invention reduce oozing, enhance adhesive performance, reduce the incidence of food occlusion and provide greater consumer confidence of product function.

The denture fixative compositions of the present invention can be formulated in powder, liquid, and cream forms that, when in contact with saliva, develop a high degree of tack and uniform viscous mucilages of high cohesive strength and that, when spread over the denture-mucosa interface, provide superior denture stabilizing properties. The compositions contain a denture fixative together with an excipient. Typical excipients include waxes and oils. Other materials often included in denture adhesives include flavoring agents, sweetening agents, viscosity modifiers, coloring agents, preservatives and thickeners. Other water soluble polymers such as xanthan gum, polyvinyl pyrrolidone (PVP), carboxymethyl cellulose, methyl cellulose and hydroxy propyl guar may also form part of the final denture adhesive formulation. Vehicles such as petroleum, mineral oil, vegetable oil and the like may form part of cream-type formulations, and non-toxic anti-caking agents such as silica, talc, dicalcium phosphate anhydrous and the like can be present. The compositions can also contain, if desired, other known denture fixatives.

While any known denture adhesive can be employed, the preferred denture adhesive employed in the composition is a partial salt of a copolymer of maleic acid or maleic anhydride and an alkyl vinyl ether. Preferably, the alkyl group has from about 1 to about 5 carbon atoms, but a more preferable copolymer includes methyl vinyl ether. As is known by those skilled in the art, the molecular weight of such copolymers can affect the properties of the copolymer and, by extension, the denture adhesive comprising the copolymer. Polymers generally do not have one precise molecular weight. Rather, polymers are made up of many polymer molecules, each having a different molecular weight. One way to measure the "average" molecular weight of a polymer is to measure its specific viscosity under specified conditions. The preferred copolymer of the invention generally has a specific viscosity (measured as a 1% weight/volume solution of methyl ethyl ketone at 25° C.) of at least about 1.5. More preferably, the specific viscosity is at least about 2.5.

The preferred copolymer of the invention is generally used as its partial salt. The maleic anhydride group can be hydrolyzed to form the corresponding dicarboxylic acid which can, in turn, react with metal compounds that partially neutralize the carboxylic acid groups on the copolymer.

Preferably less than 100% of the carboxylic acid groups on the copolymer chain are neutralized. More preferably, the metal compounds neutralize from about 50% to about 90% of the carboxylic acid groups of the copolymer and most preferably from about 65% to about 75% of the carboxylic acid groups. The preferred alkaline cations include sodium, zinc, potassium, calcium and magnesium. Preferably the salts are single or mixed salts of calcium, sodium, potassium, magnesium, zinc and zirconium. Preferred mixed salts of two cations ("double salts") include calcium/sodium, calcium/magnesium, calcium/zinc, sodium/zinc, potassium/zinc, sodium/magnesium, potassium/magnesium or calcium/potassium salts, and most preferably they are partial zinc/magnesium salts. Preferred "triple salts" of three cations include calcium/sodium/zinc and sodium/zinc/magnesium salts. A further description of the preferred adhesives can be found in the aforementioned U.S. Pat. Nos. 5,525,652 5,830,9333. In general, the adhesive active material will be about 15–60%, preferably about 25–55% of the composition.

The oils useful in the invention include without limitation mineral oil, vegetable oil such as corn, soybean, cottonseed, castor, palm and coconut oils and animal oil such as fish oil. In general, amounts of oil of about 1% to about 30% by weight of the total denture adhesive composition are usable, with amounts of about 10% to about 25% being preferred.

When a mineral oil vehicle is employed, polyethylene may be optionally used as a gelling agent to provide a "synthetic, petrolatum" vehicle, and thus is used to adjust the extrusion properties of the finished composition. Polyisobutylene may also be used in conjunction with polyethylene to further enhance the viscosity properties of the vehicle. Alternatively, a stock petrolatum, with or without mineral oil, may be employed depending on the specific handling qualities that are desired in the final product. A particularly preferred combination involves use of petrolatum in amounts of about 10% to about 40%, and a light or heavy mineral oil in amounts of about 5% to about 30% by weight of the denture adhesive composition in order to have an easily extrudable formulation having a cream-like consistence. A more preferred combination involves use of petrolatum in amounts of about 20% to about 30%, and a light or heavy mineral oil in amounts of about 10% to about 20% by weight of the denture adhesive composition.

Waxes may be added to the petrolatum, either during preparation of the denture adhesive or to form a petrolatum premix. Such waxes may be natural or synthetic waxes including, without limitation, microcrystalline waxes. When used, amounts of generally about 1% to about 25% by weight of the total denture adhesive composition are usable, with amounts of about 10% to about 25% being preferred.

The colorants useful in the present invention include pigments such as titanium dioxide, and may also include the lakes of dyes suitable for food, drug and cosmetic applications. These colorants are known as D&C dyes. Two preferred colorants are the lakes of D&C Red No. 7 and D&C Red No. 30.

Fumed silica can also be used as a thickener for the adhesive. A fine white powder, fumed silica is the colloidal form of silica (silicon dioxide, $SiO_2$) made by the combustion of silicon tetra-chloride in a hydrogen-oxygen furnace. The amount of fumed silica used in the composition may range from about 0.7% to about 2%. The amount is important since it was found that above 2% the viscosity increases to such an extent that the cream adhesive becomes much more difficult to extrude from the tube and the stability of the cream, at elevated temperatures becomes a problem.

The dental adhesive compositions of the present invention may further comprise a water-soluble cellulosic polymer as is known in the art such as methyl cellulose, carboxymethyl cellulose, sodium carboxymethyl cellulose, hydroxy propyl methyl cellulose and the like. The cellulosic polymer, preferably sodium carboxymethyl cellulose, is a powder which when moistened, becomes hydrated and tacky or gummy thereby providing additional adhesive functionality to the dental adhesive composition. The carboxymethyl cellulose gums are water-soluble, anionic long chain polymers whose properties vary to some extent depending on the number of carboxymethyl groups that are substituted per anhydroglucose unit in each cellulose molecule. These cellulose polymers comprise from about 15% to about 35%, and preferably from about 17% to about 28% of the dental adhesive composition.

The activator in the invention is a polymeric activator. Although the term "polymeric" usually means a material having hundreds, or even thousands, of repeating monomeric units, the term "polymeric" as used herein is intended to encompass materials comprising more than about seven carbon atoms and materials having a carbon "backbone" of more than three carbon atoms. Thus, for example, citric acid, having six carbon atoms and a "backbone" of five carbon atoms (including the terminal carboxylic acid groups) is not within the scope of the invention. Preferably, the activator comprises more traditional polymers, including relatively short chain resins and longer polymers, copolymers, graft or block copolymers, and linear or network polymers. Such materials can be naturally-occurring or derived or entirely artificial. Preferred materials include chelating polymeric acids and salts. Preferred chelating acids and salts comprise copolymers of dicarboxylic materials such as methyl-vinyl ether/maleic anhydride copolymers and acrylic acid/maleic acid copolymers.

A preferred polymeric activator is a polymeric acid or salt, such as a lower alkyl vinyl ether-maleic acid copolymer. This polymeric acid consists essentially of the repeated structural unit:

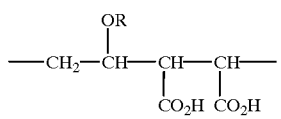

wherein R represents an alkyl radical of 1 to 4 carbon atoms, preferably methyl.

The lower alkyl vinyl ether-maleic acid polymers are readily obtained by polymerizing a lower alkyl vinyl ether monomer, such as methyl vinyl ether, ethyl vinyl ether, divinyl ether, propyl vinyl ether and isobutyl vinyl ether, with maleic anhydride to yield the corresponding lower alkyl vinyl ether-maleic anhydride polymer which is readily hydrolyzable to the acid polymer. Both anhydride and acid forms are also available from commercial suppliers. For example, the ISP Corporation, provides both the polymeric free acid form and the corresponding anhydride form under its "GANTREZ" trademark as the "GANTREZ S Series" and "GANTREZ AN Series," respectively. Daicel also provides an anhydride form under the trademark "VEMA." The GANTREZ S-97 acid is particularly suitable. When the anhydride polymer dissolves in water, the anhydride linkage is cleaved so that the highly polar, polymeric free acid is formed. Accordingly, the anhydride form, which is relatively less expensive than the acid form, may be used as a convenient and cheaper precursor for the acid. Elevated temperatures may be advantageously employed to enhance the rate of anhydride-to-acid hydrolysis.

Surprisingly, we have been unable to demonstrate that certain other polymeric acids work in the invention. For example, alginic acid (or a salt thereof), also known as polymannuronic acid, does not appear to offer the benefits of the invention. Alginic acid is commercially available and is a linear polymer of α-(1-4)-D-mannosyluronic acid and α-(1-4)-L-gulosyluronic acid residues, the relative proportion of which vary with the botanical source and state of maturation of the plant.

Moreover, other acid or acid salt additives in denture adhesives, such as sodium carboxymethyl cellulose ("CMC"), do not seem to act as activators within the invention. Accordingly, non-chelating polyacrylic acids, such as Carbopol, would not be expected to work, either.

Preferred salt cations for the activators include nontoxic cations, preferably sodium or potassium cations.

In one embodiment, this present invention provides a denture adhesive composition comprising a polymeric activator in an amount of up to about five percent by weight based on the total weight of the denture adhesive composition. In the absence of polymeric activator from the composition of this invention, compositions may be prepared that do not exhibit the enhanced effect achieved from the composition of the claimed invention. This is a surprising result because denture adhesives may already contain polymeric acid salts as part of a partial salt as discussed above. The denture adhesives of the invention, however, only exhibit the improved effect upon addition of free polymeric activator.

Preferably, the polymeric activator is present in an amount of up to about 3% by weight based on the total weight of the denture adhesive composition. More preferably, the polymeric acid is present in an amount of about 0.1 percent to about 1.5 percent by weight, and most preferably about 1 percent by weight based on the total weight of the denture adhesive composition.

In a preferred embodiment of the invention, the denture adhesive composition comprises the Mg/Zn/Na or Ca/Na or Ca/Zn partial salt of a lower alkyl vinyl ether-maleic acid copolymer, wherein the lower alkyl vinyl ether-maleic acid is present in an amount of up to about 3 percent by weight based on the total weight of the denture adhesive composition. More preferably, the lower alkyl vinyl ether-maleic acid is present in an amount of about 0.1 percent to about 1.5 percent, and most preferably about 1 percent by weight based on the total weight of the denture adhesive composition, and the lower alkyl groups are methyl. Other preferred copolymers include acrylic/maleic acid or anhydride copolymers.

The invention also provides for a method of preparing a denture adhesive composition comprising: preparing a mixture which comprises a polymeric activator in an amount of up to about 3 percent by weight based on the total weight of the denture adhesive composition; forming a denture adhesive composition including said mixture; and recovering said denture adhesive composition.

Preferably, the polymeric activator is present in an amount of about 0.1 percent to about 1.5 percent by weight based on the total weight of the denture adhesive composition being prepared. More preferably, the polymeric activator is present in an amount of about 1 percent by weight based on the total weight of the denture adhesive composition being prepared.

The invention further provides a method of preparing a denture adhesive composition comprising: preparing a mixture which comprises either the Mg/Zn/Na or the Ca/Na or the Ca/Zn partial salt of a lower alkyl vinyl ether-maleic acid mixed salt and lower alkyl vinyl ether-maleic acid, wherein the lower alkyl vinyl ether-maleic acid is present in an amount of up to about 3 percent by weight based on the total weight of the denture adhesive composition; forming a denture adhesive composition including said mixture; and recovering said denture adhesive composition.

Preferably, the lower alkyl vinyl ether-maleic acid is present in an amount of about 0.1 percent to about 1.5 percent by weight based on the total weight of the denture adhesive composition. More preferably, the lower alkyl vinyl ether-maleic acid is present in an amount of about 1 percent by weight based on the total weight of the denture adhesive composition.

The method for preparing the denture adhesive compositions may be conveniently carried out by mixing the components until a homogeneous mixture is obtained and recovering the resulting product. Preferably, the base composition is prepared as a preblended formulation that can be mixed with the remaining components used to prepare the final formulation. Mixing is conveniently performed at temperatures suitable to melt the components to be blended. For example, if polyethylene and mineral oil are to be employed, such material may be heated to temperatures from about 90° C. to 95° C., and are preferably cooled prior to blending with other components such as the polymeric acid and coloring agents.

The present invention also provides a method of making a denture adhesive composition more adhesive and less oozing, comprising adding to said denture adhesive composition a polymeric activator in an amount of up to about 3 percent by weight based on the total weight of the denture adhesive base. The polymeric activator is optionally in a finely divided powder form.

Preferably, the polymeric activator is added in an amount of about 0.1 percent to about 1.5 percent by weight based on the total weight of the denture adhesive composition. More preferably, the polymeric acid is added in an amount of about 1 percent by weight based on the total weight of the denture adhesive composition.

Optionally, the adhesive base composition to which the polymeric activator is added comprises a mixed partial salt of a chelating polymer acid. The mixed salt may be a double salt such as a Ca/Na salt or a triple salt such as a Mg/Zn/Na lower alkyl vinyl ether-maleic acid partial salt.

Whether formulated as a powder, liquid or cream, the denture adhesive compositions of the present invention hydrate to form adhesive compositions when applied to moist dentures or exposed to water.

In order to further illustrate the present invention, various illustrative examples are set forth below. In these examples, as well as throughout the specification and claims, all parts and percentages are by weight and all temperatures in degrees Celsius unless otherwise specified.

EXAMPLE 1

This example demonstrates the preparation of a denture adhesive formulation according to the invention.

A cream type denture adhesive was prepared by blending together in a Hobart type mixer the following:

| Component | Units (Weight Percent) |
|---|---|
| Mineral oil, heavy | 16.00% |
| Petrolatum | 27.85% |
| Fumed Silica | 1.10% |
| Mixed partial Mg/Zn/Na salt of MVE/MA | 30.00% |
| Sodium Carboxymethyl Cellulose | 24.00% |
| Red No. 7 Lake | 0.02% |
| Red No. 30 Lake | 0.03% |
| GANTREZ acid S-97 | 1.00% |
| Total | 100.00% |

The fumed silica is added gradually to a dispersion of the petrolatum in mineral oil at 70° C. Once the fumed silica has been uniformly dispersed, the GANTREZ salt is slowly added to the mix, followed by the sodium carboxymethyl cellulose. Once the GANTREZ salt and the sodium carboxymethyl cellulose have been thoroughly blended in, the temperature of the mix is lowered to 65° C. and the dyes are added followed by the GANTREZ acid S-97 (lower alkyl vinyl ether-maleic acid polymer). The adhesive is mixed for 30 additional minutes and then it is cooled to room temperature and discharged.

The mixed partial salt is prepared as follows. 900.40 grams of room temperature purified water were charged into a main reaction kettle equipped with a high speed stirrer. 76.26 grams of anhydrous MVE/MA copolymer were added to the main mix kettle, with continuous mixing. 250.11 grams of purified room temperature water were charged into a secondary kettle, and 3.91 grams of NaOH; 15.89 grams of ZnO and 3.94 grams of MgO were added slowly. All inorganic materials used as ingredients in the examples herein are NF or USP grade anhydrous raw materials, unless otherwise noted. The secondary kettle was well mixed to form a homogeneous slurry. This slurry was added into the main reaction kettle while mixing, then the temperature of the reaction was raised to 85–90° C. and held at that temperature for two hours. The resulting dispersion was cooled to room temperature and poured into shallow stainless steel drying trays, and the trays were placed in a hot air convection oven at 70° C., for 18–20 hours to give a dried salt. Although trays were used in this example, a drum drier would also be acceptable.

The dried Mg/Zn/Na Gantrez salt was then milled through a suitable mill and screened through a #100 mesh sieve. A one percent solution of the resulting powder would have a pH of from about 5 to about 7. This salt is a 10% Na/40% Zn/20% Mg salt of MVE/MA copolymer.

EXAMPLE 2

Comparative

A cream adhesive is prepared exactly as shown in example 1, except that the GANTREZ Acid S-97 addition is omitted.

When tested, the denture adhesive formulations prepared according to example 1 provided enhanced adhesive performance, reduced oozing and incidence of food occlusion over the denture adhesive formulation of example 2.

EXAMPLE 3

A cream adhesive is prepared exactly as shown in example 1, except that Sokalan C5 is used instead of GANTREZ Acid S-97.

EXAMPLE 4

A cream adhesive is prepared exactly as shown in example 1 except that it contains 0.5% GANTREZ Acid S-97.

While specific examples of materials, compositions and processes have been described and illustrated, it will be apparent to those skilled in the art that a wide variety of changes and modifications may be made and still be within the broadest aspects of this invention. It should be understood that the examples and the particular proportions and methods of procedure set forth are intended to be illustrative only.

What is claimed is:

1. A denture adhesive composition consisting essentially of a denture adhesive effective amount of a denture adhesive polymer salt and a pharmacologically acceptable carrier therefor and a polymeric activator in an amount of up to about 3 percent by weight based on the total weight of the denture adhesive composition, wherein said polymeric activator is the sodium or potassium partial salt of a polymeric acid containing a repeating unit which has at least seven carbon atoms and more than three carbon atoms in its backbone and is not the same as any component of the denture adhesive salt polymer.

2. The denture adhesive composition of claim 1, wherein said polymeric activator is present in an amount of about 0.1 percent to about 1.5 percent by weight based on the total weight of the denture adhesive composition.

3. The denture adhesive composition of claim 2, wherein said polymeric activator is present in an amount of about 1 percent by weight based on the total weight of the denture adhesive composition.

4. The denture adhesive composition of claim 1, wherein said polymeric activator is a potassium partial salt of a lower alkyl vinyl ether-maleic acid copolymer.

5. The denture adhesive composition of claim 1, in which the denture adhesive salt is a mixed partial salt of a copolymer of maleic acid and an alkyl vinyl ether and at least one cation, wherein all of said cations are selected from the group consisting of sodium, potassium, calcium, magnesium, zinc and zirconium cations.

6. The denture adhesive composition of claim 5, wherein one of said cations is a sodium cation and the alkyl moiety is methyl.

7. The denture adhesive composition of claim 1, wherein said polymeric activator is a sodium partial salt of a lower alkyl vinyl ether-maleic acid copolymer.

* * * * *